United States Patent
Lamb

(10) Patent No.: US 8,527,063 B2
(45) Date of Patent: Sep. 3, 2013

(54) SYSTEM AND METHOD FOR HYPERTHERMIC TUMOR TREATMENT

(76) Inventor: Karl J. Lamb, Port Angeles, WA (US)

(*) Notice: Subject to any disclaimer, the term of this patent is extended or adjusted under 35 U.S.C. 154(b) by 280 days.

(21) Appl. No.: 12/833,196

(22) Filed: Jul. 9, 2010

(65) Prior Publication Data

US 2012/0010454 A1 Jan. 12, 2012

(51) Int. Cl.
- *A61F 2/00* (2006.01)
- *A61F 7/12* (2006.01)
- *A61N 2/00* (2006.01)
- *A61M 37/00* (2006.01)

(52) U.S. Cl.
USPC .............. 607/103; 600/10; 600/12; 219/635; 607/113

(58) Field of Classification Search
USPC .............. 607/113, 103; 600/12, 10; 219/635
See application file for complete search history.

(56) References Cited

U.S. PATENT DOCUMENTS

| | | | |
|---|---|---|---|
| 4,537,181 A | 8/1985 | Shalhoob et al. | |
| 5,197,940 A * | 3/1993 | Sievert et al. | 600/9 |
| 5,342,283 A | 8/1994 | Good | |
| 6,344,272 B1 | 2/2002 | Oldenberg et al. | |
| 7,627,381 B2 | 12/2009 | Kanzius et al. | |
| 2006/0030914 A1 | 2/2006 | Eggers et al. | |
| 2006/0142748 A1 | 6/2006 | Foreman et al. | |
| 2007/0083074 A1* | 4/2007 | Sotiriou | 600/8 |
| 2011/0052672 A1 | 3/2011 | Krishnan et al. | |
| 2011/0224479 A1* | 9/2011 | Yager | 600/10 |
| 2012/0010454 A1 | 1/2012 | Lamb | |

OTHER PUBLICATIONS

U.S. Appl. No. 12/833,207, filed Jul. 9, 2010, Karl J. Lamb.
Korean Intellectual Property Office; International Search Report; Feb. 28, 2012; Seo-gu, Daeieon—Republic of Korea.
Vilhelm Ekstrand et al.; Influence of Electrical and Thermal Properties on RF Ablation of Breast Cancer. Is the Tumor Preferentially Heated?; Biomed. Eng. Online; Jul. 11, 2005; Http://www.ncbi.nlm.gov/pmc/articles/PMC1188061/(1of20).

* cited by examiner

*Primary Examiner* — Linda Dvorak
*Assistant Examiner* — Jared W Pike
(74) *Attorney, Agent, or Firm* — Michael J. Donohue; Davis Wright Tremaine LLP

(57) ABSTRACT

A system to induce hyperthermia in a selected portion of the body utilizes permanent magnets mounted on a variable speed motor. A conductive button is positioned at a location proximate the target tissue to be heated, such as a tumor. The magnetic rotor assembly is positioned at a selected distance from the conductive button and rotated at a desired frequency to produce a changing permanent magnetic field that induces an eddy current on the surface of the conductive button. A temperature sensor may be positioned near the conductive button as a feedback mechanism to a control circuit. At higher magnetic polarity frequencies, the conductive button may be implemented in the form of metallic nanoparticles. In this embodiment, the nanoparticles may include molecular elements that selectively bind with the target tissue and thereby accumulate at the target tissue prior to the introduction of the rotating magnetic field.

26 Claims, 9 Drawing Sheets

SYSTEM AND METHOD FOR HYPERTHERMIC TUMOR TREATMENT

BACKGROUND OF THE INVENTION

1. Field of the Invention

The present invention is directed generally to the hyperthermic treatment of cancer, and, more particularly, to a system and method for hyperthermic treatment using permanent magnets.

2. Description of the Related Art

The human body uses heat to fight disease, naturally. This phenomenon is called fever. The higher temperature increases metabolic activity and allows the body to fight the disease more effectively.

In a similar fashion, researchers are using heat to attack cancer cells. According to the National Cancer Institute, hyperthermia cancer treatment kills cancerous cells by elevating their temperatures to a therapeutic range of 108°-113° Fahrenheit (° F.). Hyperthermia is a well known thermal therapy wherein the cytotoxic effects of elevated temperatures in tissue are induced to achieve cell death or render the cells more vulnerable to ionizing radiation or chemical toxins.

Many new technologies are being developed to address the need to cure diseases in humans and animals, especially in the field of Oncology. Treatments ranging from Hyperthermia to Radiation are being offered either individually or in conjunction with each other to combat the disease at its source, the tumor and cancerous cells. Efforts to develop ways to target localized heat to affected areas of the body and skin range from Radio Frequency (RF) ablation, Microwave Hyperthermia, X-ray and Magnetite Hysteresis.

These prior art technologies all use different types of electromagnetic waves. The higher the energy of the particles of electromagnetic waves the shorter the wavelength, with x-rays being the shortest and radio waves the longest. Electromagnetic waves travel through any material as well as through a vacuum. When electromagnetic waves hit an object, they slow down as their energy decreases and the wavelength becomes longer, generating heat at the surface of the object that in turn causes the particles of that object to vibrate.

The heat and vibration of the particles depends on the wavelength and energy of the electromagnetic wave and relates directly to the heat sources for the above mentioned treatments. Electromagnetic (radio frequency and microwave) devices are adjusted by controlling their power supply and frequencies. These parameters must be recalculated for each treatment session to reduce the margin of errors.

The downsides of these prior art technologies can be numerous. With RF ablation if the temperature is too high, vaporization and charring limit the effective volume of tissue that may be treated. Nearby blood vessels may also affect treatment by acting as a heat sink to cool the diseased site, or by diverting energy away from the target acting as energy sink because blood is more thermally conductive than other tissues. Microwave hyperthermia energy applied externally can cause surface burns and blisters and damage tissues between the treatment site and the body's surface. Metallic implants within the patient may also become excessively heated by the microwaves. Magnetite Hysteresis is hampered by a lack of cellular selectivity and by characteristically uneven distribution. Further downsides include the limited ability to treat the diseased area from distances greater than 0.1" (inches) deep due to the expanding exposure of unwanted energy in the surrounding soft tissues and blood.

The common difficulty with RF and microwave heat treatments seems to center in delivering repeatable, controllable heat to the desired diseased site without causing negative effects to the surrounding surface and soft tissues. This task is made more difficult by the varying density and water content of various tissues ranging from blood to bone and the preferential heat absorption and electrical conductivity of each type of tissue. There is also significant complication with delivering the required heat deep within the body as the microwave energy is significantly disbursed before it gets to the target. Unfortunately healthy tissues also absorb microwave, laser, and ultrasound energy. These factors are significant because each treatment site for each patient requires careful calculation of its own set of parameters for safety and effectiveness.

Therefore, it can be appreciated that there is a significant need for techniques for hyperthermic treatment that reduces side effects and non-desirable heating and may be controlled in a predictable, repeatable fashion. The present invention provides this, and other advantages, as will be apparent from the following detailed description and accompanying figures.

BRIEF DESCRIPTION OF THE SEVERAL VIEWS OF THE DRAWING(S)

DETAILED DESCRIPTION OF THE INVENTION

The present invention improves upon prior art technologies by utilizing a passive permanent magnet field with no wavelength. The present disclosure describes safe, repeatable, and controllable techniques to deliver localized homogenous heat at a distance to a diseased site while avoiding the introduction of auxiliary foci in normal tissue.

The system disclosed herein utilizes rotating high strength permanent magnets in conjunction with highly conductive "target button." The target button is strategically placed and orientated on the skin or in the body in the region where localized homogenous heat is desired to treat cancerous cells or tumors.

A rotating permanent magnet rotor, separated by a distance from the target button, causes localized heating of the target button in the region proximate the tumor. The permanent magnet field source is always "on" and remains constant, predictable and repeatable. Electromagnetic fields are created by electrical energy and are turned 'on and off' with the flow of electrical power. A unique feature of permanent magnet fields is their ability to act as transducers, transforming energy from one form to another, without any permanent loss of their own energy. The use and control of passive permanent magnet fields may be considered as more of a physical/mechanical process rather than an electronic process. The magnetic fields generated by permanent magnets also differ from those of electromagnetic fields in that permanent magnet fields will pass through the body's tissues and bone without affecting them, without creating heat in unwanted areas or otherwise causing damage.

Figure 1:
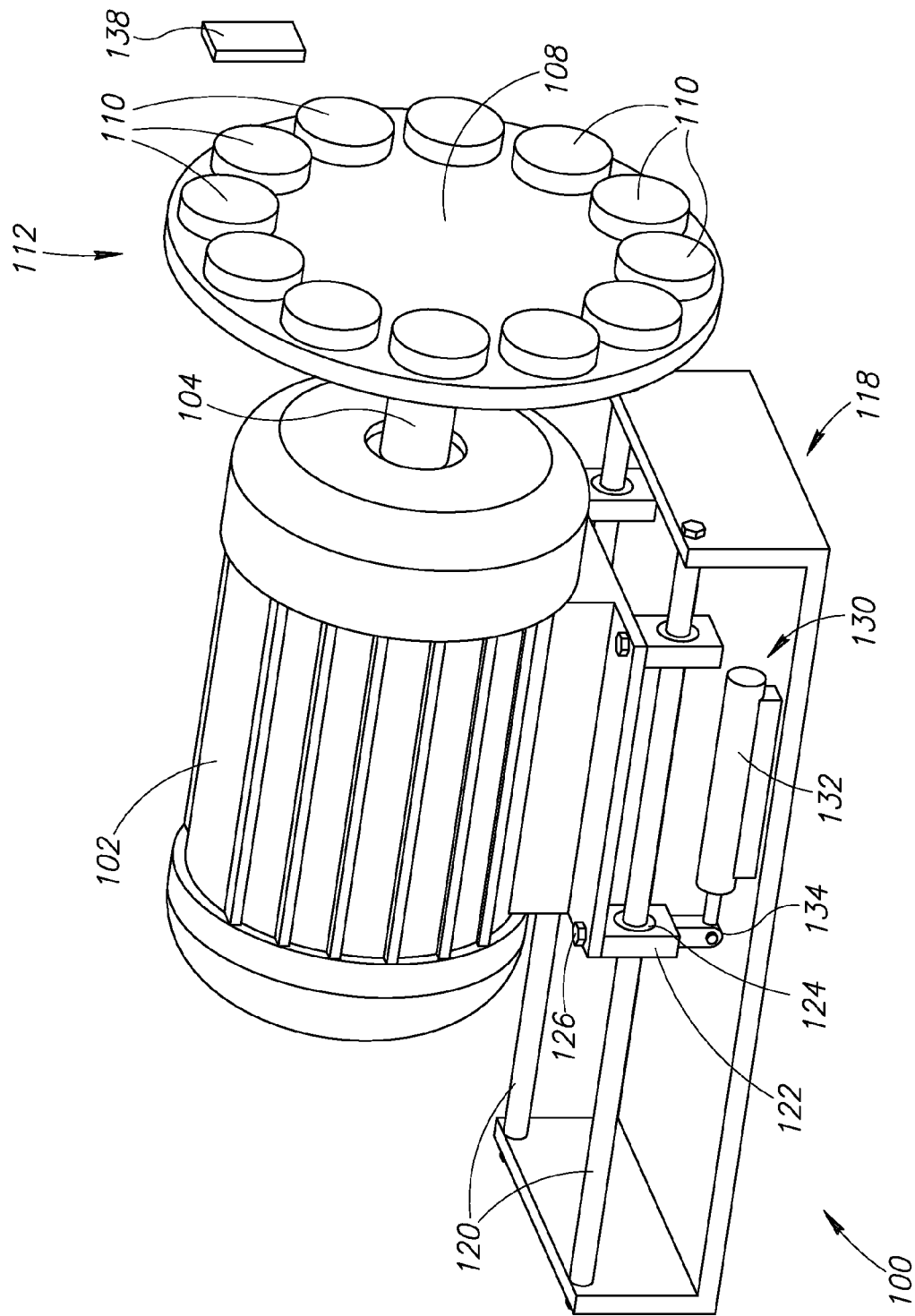
FIG. 1 is a perspective view of a treatment system constructed in accordance with the present teachings.

In an exemplary embodiment, the present invention is illustrated as a system 100 in FIG. 1 and includes a variable speed motor 102 having a motor shaft 104. The motor shaft 104 includes a shaft key 106 (see FIG. 3) to secure a plate or disk 108 to permit the disk to rotate with the motor shaft. Mounted on a surface of the disk 108 are a plurality of high strength permanent magnets 110 that are configured in an N-S-N-S polarity arrangement spaced about the disk to form a magnetic rotor assembly 112. In an exemplary embodiment, the permanent magnets 110 are Neodymium or Samarium Cobalt permanent magnets.

The number of magnets 110 attached to the plate 108 may vary depending on the size of the plate and on the particular application.

A frame 118 is used to support the motor 102 and to permit positioning of the magnetic rotor assembly 112 in the desired position near the patient. The motor 102 is slide-mounted on a linear rail 120 of the frame 118 to allow proper positioning of the magnetic rotor assembly 112. The motor 102 is mounted to the linear rail 120 using slide blocks 122 having bushings 124 and attached with bolts 126 to the feet of the motor 102. A positioning system 130 is attached to the frame 118 to permit the motor 102 to slide back and forth along the linear rail 120. The positioning system 130 includes an actuator 132 and a rod end 134 coupled to one of the slide blocks 122. The actuator 132 may be mechanically adjusted, or may be implemented as an electrical actuator, hydraulic actuator, pneumatic actuator, or the like.

The positioning system 130 serves to control the position of the magnetic rotor assembly 112 in an axial direction to thereby selectively control the distance between the magnets 110 and a conductive button 138. As will be described in greater detail below, the conductive button 138 is strategically positioned on the skin or within the body near a tumor or cells and responds to the rotating permanent magnetic fields through the generation of heat in a controllable fashion.

The rotating magnets 110 interact with the conductive button 138 to produce eddy currents on the surface of the conductive button. Eddy currents, like all electric currents, generate heat. Eddy currents on the surface of the conductive button 138 generate resistive losses that transform rotating magnetic energy into heat. Those skilled in the art will appreciate that the rotating magnetic fields change polarity of the field at the surface of the conductive button 138 thus inducing eddy currents and generating heat.

The amount of heat generated at the surface of the conductive button 138 depends on a number of factors, each of which can be controlled by the system 100. First, the strength of the permanent magnets 110 have a direct effect on the amount of heat generated by the conductive button 138. That is, the gauss flux density at the conductive surface of the conductive button 138 depends directly on the magnetic field generated by the magnets 110. While it is not convenient to switch magnets on the magnetic rotor assembly 112, those skilled in the art will appreciate that a small version of the system 100 may use less powerful magnets for treatment of tumor at or near the surface of the skin. In contrast, a larger version of the system 100 may use more powerful magnets to penetrate deep within the body.

Varying the distance between the magnets 110 and the conductive button 138 also affects the heat generated by the conductive button. The amount of heat generated at the surface of the conductive button 138 varies inversely with the distance. That is, the greater the distance between the magnets 110 and the conductive button 138, the lower the gauss flux density and, therefore, the lower the temperature produced at the surface of the conductive button.

In addition, the rate of change of the magnetic poles has a direct effect on the heat produced by the conductive button 138. As noted above, the motor 102 is a variable speed motor. Varying the speed of the motor 102 controls the number of North to South magnetic polarity changes. This may be referred to as the magnetic polarity frequency between the magnets 110 and the conductive button 138. That is, a change from N-S-N in the magnetic field at the surface of the conductive button 138 may be considered a magnetic polarity cycle. As the disk 108 rotates, the conductive button 138 is exposed to a number of magnetic polarity changes each minute based on the speed of the motor 102 and the number of magnets 110 mounted on the disk 108.

By varying the speed of the motor 102 and the distance between the magnets 110 and the conductive button 138, the system 100 can accurately control the temperature in the tissues surrounding the conductive button 138. As will be discussed in detail below, the strength of the magnetic field generated by the magnets 110 can also be used to control the amount of heating at a distance. For example, if the cancerous area is skin cancer, the conductive button 138 may be placed on the surface of the body at the desired level of heat generated by relatively low strength magnets. If the cancerous cells are deep within the body, a larger magnetic assembly, having more powerful magnets 110 may be used to generate the desired heating at a greater distance.

The system 100 uses permanent magnet rotors that rotate from a distance (without physical contact with the target or body) from the conductive button 138 to generate a controllable, repeatable and predictable homogenous heat source only affecting the localized treatment area of the conductive button. The system 100 greatly improves the distance from source (i.e. the permanent magnets 110) to target (i.e., the conductive button 138) due to the use of high strength Neodymium or Samarium Cobalt permanent magnets. High strength permanent magnets can exhibit flux densities sufficient to act upon the conductive buttons at distances from 0.3" using one small magnet rotor to a distance greater than 6.0" using two large magnetic rotor assemblies 112 (see FIG. 4). The number of magnetic poles for each magnet rotor is important relative to the speed of the magnet rotor. It has been shown that a higher magnetic polarity frequency can induce diamagnetic heat in the conductive button 138 at greater distances allowing for yet another means to control the homogenous heat generation.

The simplicity of the system 100 permits a safe, low cost option for new localized Hyperthermia treatment options using simplified operating parameters and the present system 100 is scalable as needed.

The system provides homogenous heat in the conductive button 138 to a diseased site while avoiding the introduction of auxiliary foci in normal tissue due in nature to the passive permanent magnet field. The system 100 can selectively change the distance and/or speed of the magnetic rotor assembly 112 relative to the conductive button 138 to control the homogenous heat delivered to the diseased area. The system 100 controls the homogenous heat in the conductive button 138 to within 0.01° F. in a range from as low as 1° above body temperature to as high as 350° if desired.

The rotational speed of the motor 102 and number of magnetic poles of the magnets 110 determines the magnetic polarity frequency acting upon the conductive button 138, controlling the homogenous heat for a given distance. The system 100 has successfully been tested at magnetic polar frequencies as low as 229 Hz and up to 993 Hz. It should be appreciated by one skilled in the art that even higher polarity frequencies will provide even greater distances enabling placement of the conductive button 138 at a deeper depth into the body, for example. In addition, tests have confirmed that higher magnetic polar frequencies are effective on smaller size conductive buttons 138. This will be described in greater detail below.

Figure 2A:
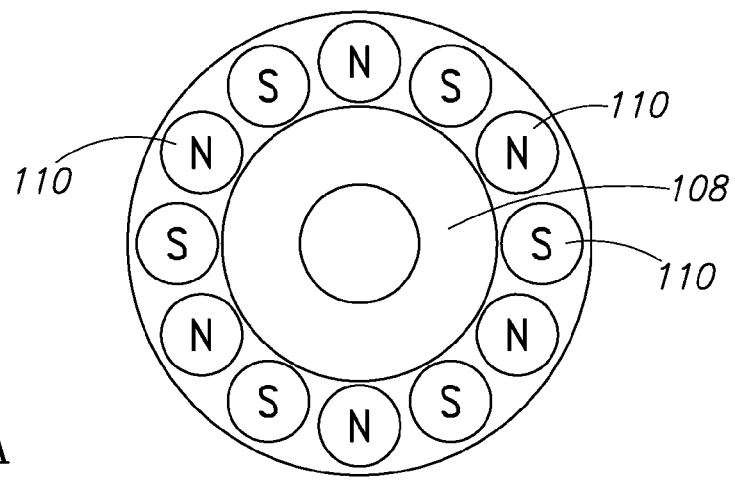
FIGS. 2A-2C illustrate a number of different embodiments for the permanent magnetic arrangement in the system of FIG. 1.
Figure 2B:
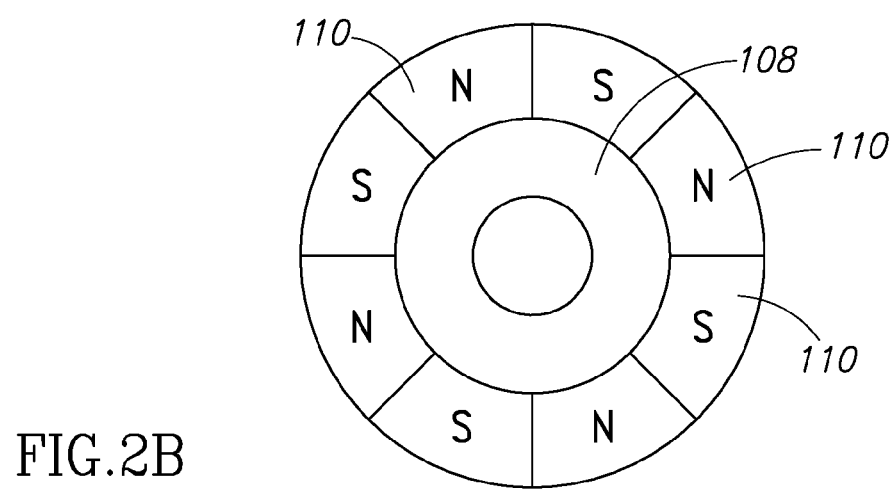
Figure 2C:
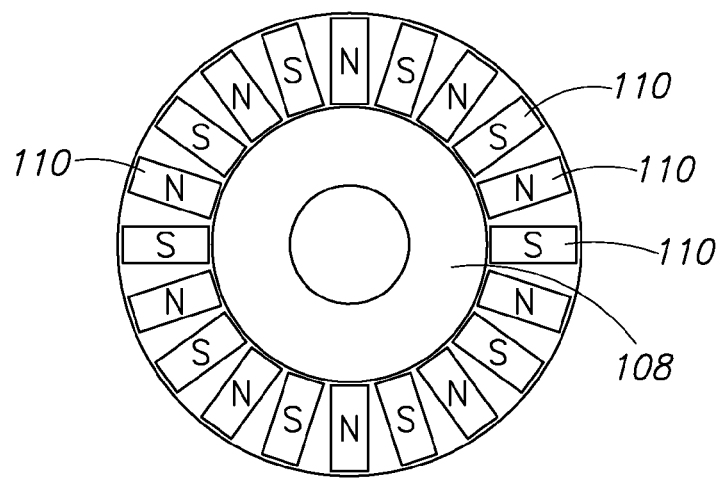

In FIG. 2 it can be appreciated to those in the art that various shapes of magnet 110 can make up a magnet rotor assembly 112 using round magnets shown in FIG. 2A, or rectangular magnets, as shown in FIG. 2C. Alternatively, the magnets 110 may be implemented as a solid magnetic disk with multiple magnetic poles, as illustrated in FIG. 2B. As described above, the magnets 110 are mounted to the disk 108. In an exemplary embodiment, the disk 108 is a steel plate. Those skilled in the art will appreciate that the steel plate acts as a "keeper" to direct or focus the magnetic field outwardly from the magnets and away from the direction of the motor 102. In some embodiments, such as that of FIG. 2C, the magnets 110 may be mounted to an aluminum frame which, in turn, is mounted on the steel disk 108.

Figure 3:
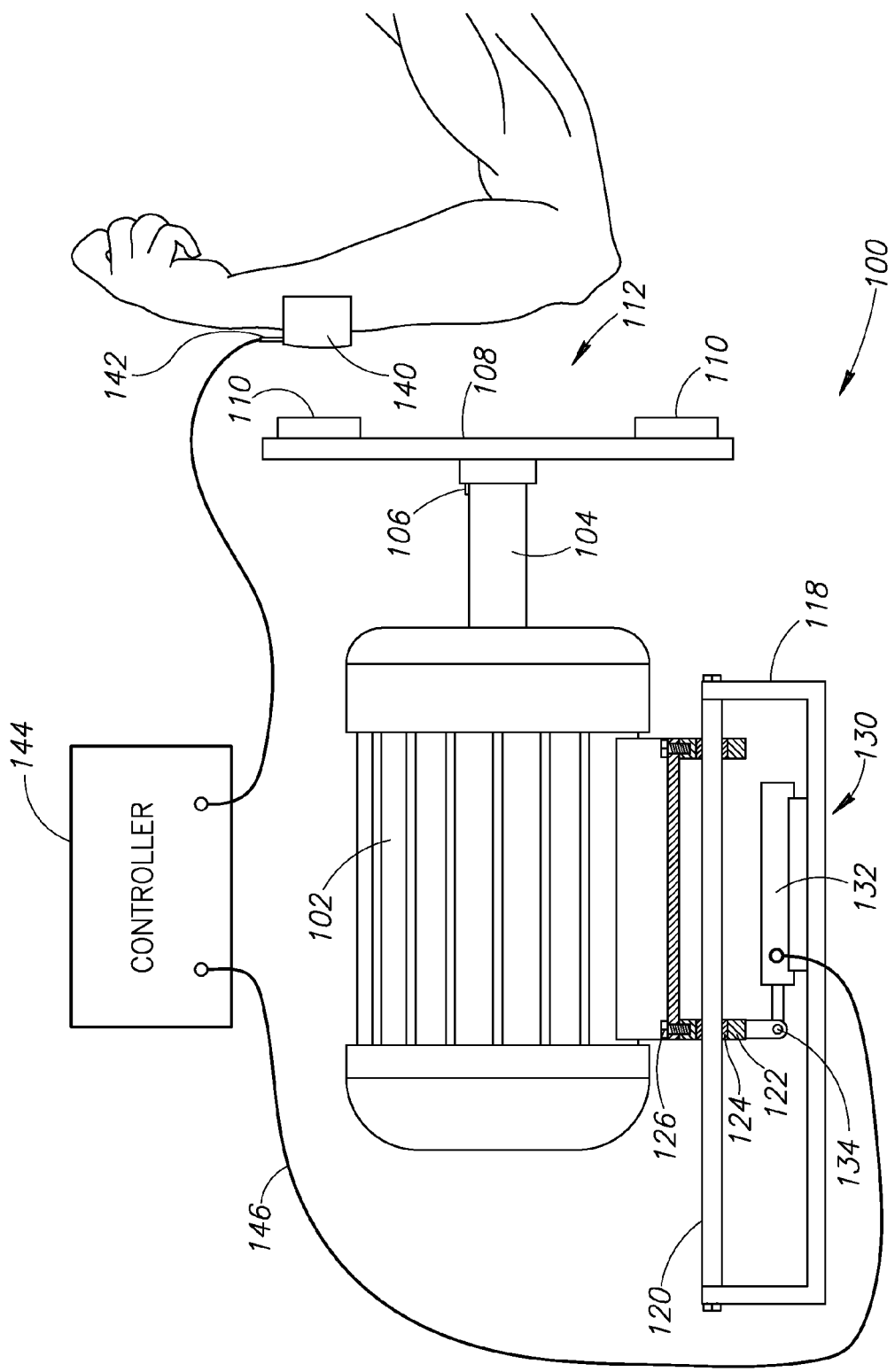
FIG. 3 illustrates the operation of the system of FIG. 1 for application of heat to a patient.

FIG. 3 illustrates the operation of the system 100 for treatment of skin cancer or tumor on the surface of the body. As illustrated in FIG. 3, the conductive button 138 may be implemented as part of a removable bandage 140. A thermocouple 142 is also positioned within the bandage 140 at a location close to the conductive button 138. The operation of a thermocouple to monitor temperature is well known in the art, and need not be describe in greater detail herein. Other forms of temperature sensing devices may also be satisfactorily employed in the system 100. The output of the thermocouple 142 is provided to a controller 144. The controller 144 may be implemented as a conventional personal computer, microprocessor microcontroller, or the like. The system 100 is not limited by any specific form used to implement the controller 144.

As illustrated in FIG. 3, the controller 144 monitors the temperature at the site of the tumor using the thermocouple 142. The controller 144 also has an output 146 to control the positioning system 130, thereby forming a closed loop control system. That is, the controller 144 monitors the temperature using the thermocouple 142 and adjusts the position of the magnets 110 using the controller output 146 to control the positioning system 130. The controller 144 may be operated by a user to select the desired temperature to be produced at the conductive button 138. The user may also enter control data into the controller 144 to establish an initial position for the magnetic rotor assembly 112 at a desired distance with the conductive button 138 in or on the patient. In one treatment protocol, the controller 144 can control the position of the magnetic rotor assembly and/or the rotational speed of the motor 102 to maintain the temperature at a desired level. In one treatment protocol, the temperature may be maintained at a constant level for a period of time. In a different protocol treatment, the temperature at the conductive button 138 may be alternated or cycled between two predetermined temperatures. In yet another treatment protocol, the temperature at the conductive button may be raised to a high temperature (e.g., 200° F.) for a short period of time and then quickly lowered. This type of treatment protocol may also be cycled between high temperature and a cooling cycle.

Figure 4:
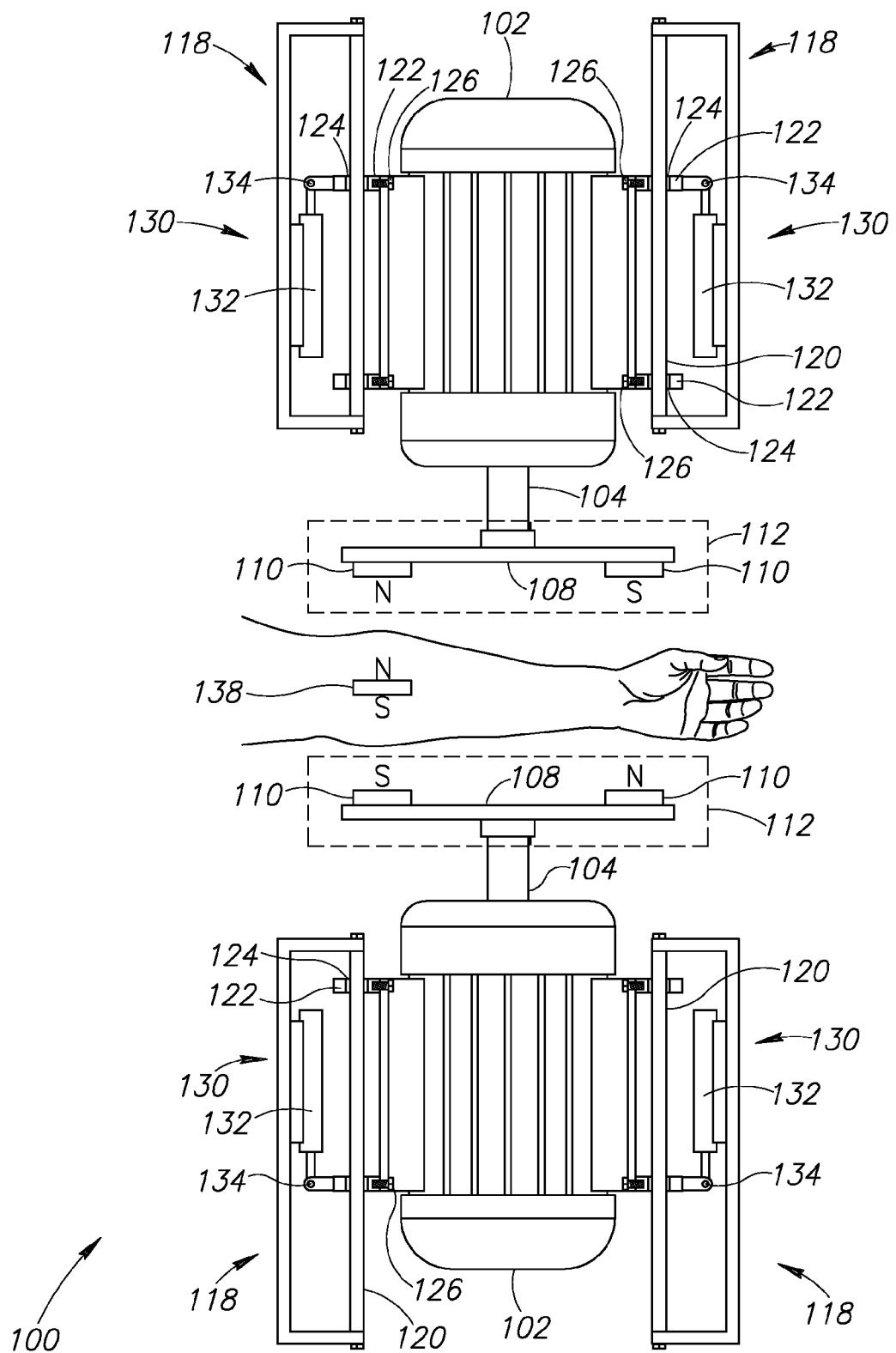
FIG. 4 illustrates an alternative embodiment to the system of FIG. 1 utilizing multiple magnetic systems.

FIG. 4 illustrates dual systems 100 operating in conjunction with each other. As illustrated in FIG. 4, one system 100 is positioned on one side of the patient with the other system positioned on the opposite side of the patient with the conductive button 138 there between. Those skilled in the art will appreciate that the powerful magnets will align the magnetic rotor assemblies 112 such that the north pole on the magnetic assembly 112 of one system 100 will align with the south pole of the magnetic assembly 112 of the other system. While electrical synchronization of the motors could be maintained using known technologies, the powerful magnets tend to align the magnetic rotor assemblies 112 and thus maintaining synchronization between the motors 102.

While FIG. 4 illustrates the operation of dual systems 100 to control heating of the conductive button 138 in an arm of the patient, this approach can also be taken to heat the conductive button deep within the body of the patient. For example, the conductive button 138 may be introduced to the site of a tumor using laparoscopic or other known surgical procedures. The dual systems 100 may be positioned on opposite sides of the patient's body. The attractive N-S and S-N polarity circuit between the dual magnetic rotor assemblies 112 produce a highly concentrated magnetic flux zone. The increased flux in the zone between the two magnetic rotary assemblies 112 provide the ability to place the conductive buttons 138 into limbs, torsos, organs, or the like reaching even deeper depths of the body. A large-scaled double magnetic rotor assembly, such as that illustrated in FIG. 4, has been tested resulting in a flux density of 1,200 gauss centered within a 2.0" air gap allowing for the system 100 to operate at distances of six inches or more from the conductive button 138.

A dual system 100 of FIG. 4 may have a very large magnetic rotor assembly that can be up to several feet in diameter. To accommodate the larger size of the magnetic rotor assembly 112 and motor 102, FIG. 4 illustrates dual frames 118 and dual positioning systems 130 for each of the motors 102. The positioning system 130 may operate in the manner described above to control the position of the magnetic rotor assembly 112 with respect to the conductive button 138. The controller 144 (see FIG. 3), may also be used in conjunction with a temperature probe, such as the thermocouple 142 to control the relative position and/or speed of the magnetic rotor assemblies 112 to generate a magnetic field sufficient to maintain temperature at a selected level.

Figure 5:
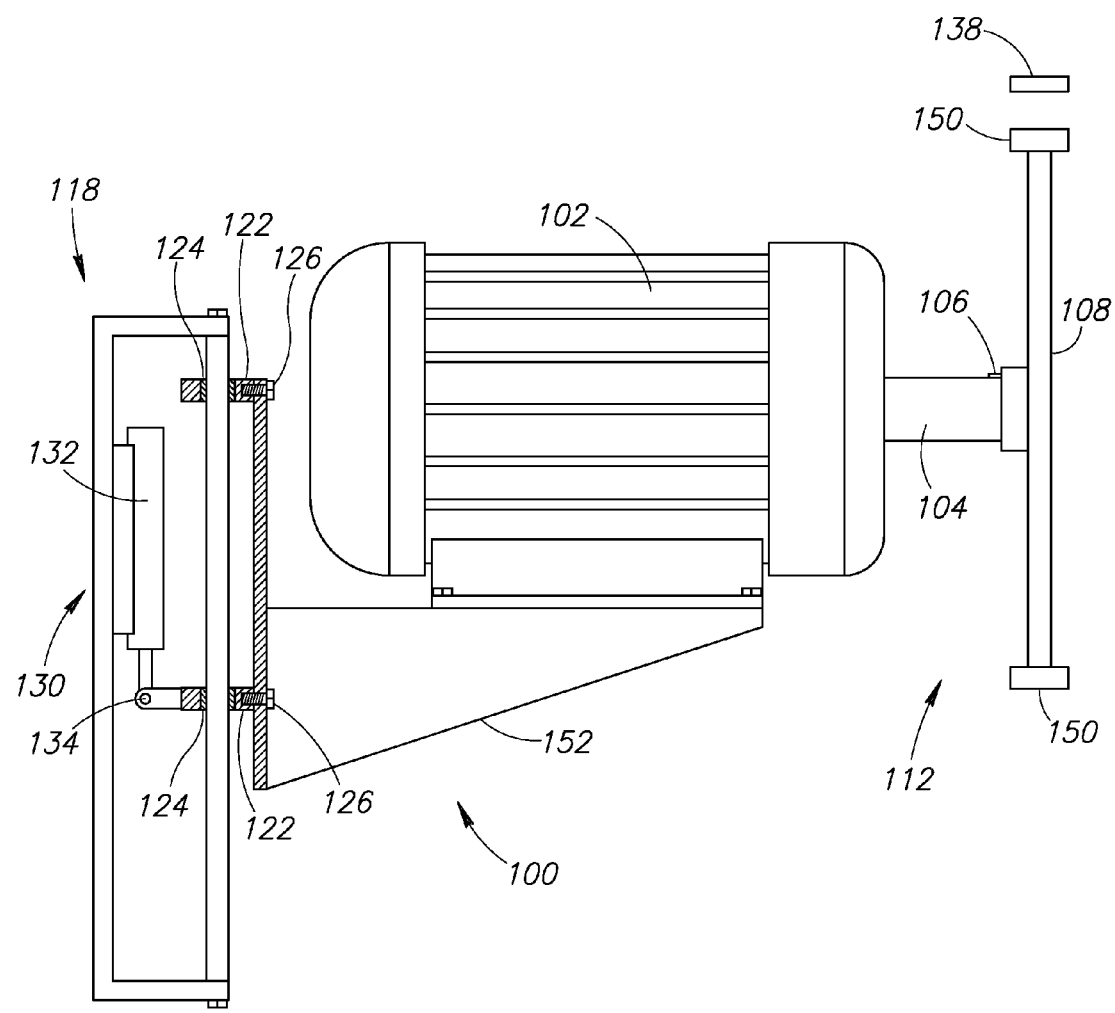
FIG. 5 illustrates another alternative embodiment to the system of FIG. 1.

FIG. 5 illustrates yet another embodiment of the system 100 in which a ring magnet 150, having its magnetic polarity pointed outwardly in a radial direction from the center of the disk 108. The ring magnets 150 are mounted to the outer rim of the disk 108. In this embodiment, the ring magnet 150 has an annular plurality of magnetic poles in an N-S-N-S arrangement. The ring magnet 150 and disk 108 are mounted to the motor shaft 104 in the manner described above. The variable speed motor is mounted to a gusset plate 152 which, in turn, is bolted to the frame 118 using the linear rail 120, slide box 122, bushings 124, and bolts 126. The system 100 illustrated in FIG. 5 operates in the manner discussed above with respect to FIG. 1 except that the distance between the ring magnets 150 and the conductive button 138 is the distance between the peripheral edge of the disk 108 and the conductive button 138. The positioning system 130 operates to position the peripheral edge of the magnetic rotor assembly 112 at a distance from the conductive button 138 to thereby maintain temperature at a selected level. The thermocouple 142 (see FIG. 3) or other temperature sensing component may be positioned proximate the conductive button 138 and used to provide feedback to the controller 144.

The system 100 demonstrates that the flux density and distance are directly related. Homogenous heat generation up to 131° F. has been achieved in the conductive button 138 with flux densities as low as 135 gauss and 229 polarity Hz within five minutes time. Homogenous heat generation as high as 350° F. has been achieved in the conductive button 138 using 1,250 gauss at 288 polarities Hz within 30 seconds time. Working distances between the face of the magnets 110 and the face of the conductive button 138 range from 0.3" with single magnetic rotor assembly 112 to over 6.00" using the dual magnet rotor assembly configuration of FIG. 4.

In the embodiments discussed above, the magnetic rotor assembly 112 (see FIG. 1) has relatively few magnets 110. However, the magnetic rotor assembly 112 can include a very large number of magnets. As discussed above with respect to FIG. 2B, the magnet 110 may be implemented as a solid magnetic disk with multiple magnetic poles. While the embodiment in FIG. 2B shows a relatively small number of magnetic poles, tests have shown that a magnetic disk may contain as many as 1,000 to 10,000 magnetic poles. The number of magnetic poles that may be implemented on a single disk is limited by the size of the disk as well as the coercivity of the magnetic material. The coercivity of a magnetic material refers to its ability to withstand de-magnetization forces that may act upon the magnetic material. Those skilled in the art will appreciate that a disk 108 with 10,000 magnetic poles must be able to withstand any de-magnetization forces that would alter the arrangement of magnetic polarities on the disk.

In this embodiment, the motor 102 is a high-speed variable motor. In an exemplary embodiment, the motor 102 may have speeds that exceed 7,200 revolutions per minute (rpm). With the motor operating at 7,200 rpm and 20,000 magnetic poles (i.e., 10,000 N poles and 10,000 S poles) in the magnetic rotor assembly 112, the system 100 can operate at magnetic polar frequencies in excess of 1 megahertz (MHz). While the system produces magnetic polarity frequencies in the radio frequency range (e.g., greater than 1.0 MHz), the magnetic rotor assembly 112 still does not produce an electric field associated with radio frequency electromagnetic waves. Thus, the system 100 does not have the side effects produced by an electromagnetic field.

Tests have shown that operation of the system 100 at higher frequencies is successful with the conductive button 138 having a much smaller size. Tests have been satisfactorily conducted showing the mass of the conductive button 138 as low as 0.005 grams. In one embodiment, the conductive button 138 was approximately 0.25" in diameter. A square conductive button 138 has been tested with dimensions as small as 0.25"×0.25" while the system 100 operates in the manner discussed above.

Relatively low magnetic polarity frequencies and a relatively high magnetic field strength appear to cause only heating effects at the conductive button 138, thus heating the surrounding tissues. With higher magnetic polarity frequencies and a relatively lower magnetic field strength, cell ablation occurs in the region surrounding the conductive button 138.

If the magnetic polar frequencies are sufficiently high, the magnetic conductive button 138 may be implemented as a collection of nanoparticles. U.S. Pat. No. 7,627,381 discloses a radio frequency induced hyperthermia using metallic nanoparticles whose size is measured in nanometers (1.0-1000 nm). In one embodiment discussed in this reference, the nanomaterials have antibodies attached thereto that cause them to bind selectively to the target cells, such as a tumor. The metallic nanoparticles are injected into the patient and will migrate to the site of the tumor and selectively attach to the tumor cells. In U.S. Pat. No. 7,627,381, the magnetic particles are placed in a pathway between a radio frequency transmitter and a radio frequency receiver and are thus exposed to the electromagnetic field generated by the radio frequency transmitter.

In contrast, the system 100 exposes the patient only to a high magnetic polarity frequency thus exposing the patient only to a magnetic field with no accompanying electric field. This avoids the side effects caused by electromagnetic radio frequency fields. In operation, the metallic nanoparticles with appropriate antibodies attached thereto are injected into the patient prior to exposure to the magnetic field generated by the system 100.

The term "antibody" as used herein refers to a protein binding component that attaches at one portion to the metallic nanoparticles and attaches to the target cell at another portion of the protein binding component. The development of such protein binding components is known in the art and need not be described in greater detail herein. The metallic nanoparticles selectively attach to the cells of the tumor or other selected target tissue. Upon exposure to the rotating magnetic field generated by the system 100, the metallic nanoparticles are heated in the manner described above. The use of magnetic polarity frequencies in excess of 1.0 MHz permits the use of very small conductive buttons 138, such as the collection of metallic nanoparticles to achieve the same outcome as a more conventional conductive button at lower magnetic polarity frequencies. That is, the accumulated metallic nanoparticles heat up in the presence of the rotating magnetic field thereby raising the temperature of the surrounding tissues. At these high magnetic polarity frequencies, tissue ablation can occur thus effectively destroying the target tissue without surgical intervention.

Example structures and operation of the system 100 has been illustrated in various embodiments. Those skilled in the art will appreciate that other alternative arrangement for rotating permanent magnets may also be used to implement the system 100.

Figure 6A:
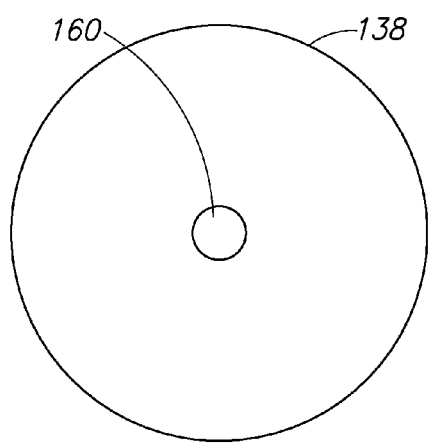
FIGS. 6A-6L illustrate different embodiments for a metallic object used for localized heating when exposed to the rotating permanent magnet system of FIG. 1.

The conductive button 138 may also be implemented in a variety of forms. FIGS. 6A-6L illustrate some of the various forms that can be used to implement the conductive button 138. Even these examples are but a few of the multitude of designs, shapes, thicknesses and through-hole configurations that can be used to implement the conductive button 138. FIG. 6A is a round conductive button. At relatively low magnetic polarity frequencies (e.g., less than 1000 Hz) the conductive button 138 in FIG. 6A may be approximately 0.5" in diameter and have a mass of approximately 1-6 grams depending on the particular material used to implement the conductive button. In early experiments, tests were conducted at relatively low magnetic polarity frequencies (e.g., less than 1000 Hz) using a variety of materials for the conductive button 138. In one embodiment, the conductive button 138 is an aluminum disk of approximately 0.5" diameter and approximately 0.145" thick. The aluminum embodiment of the conductive button 138 weighs 1.1 grams. A similar-sized copper disk weighs 3.9 grams. In one embodiment, the copper disk includes a central hole (see FIG. 6A). The copper disk with a central hole weighed approximately 3.1 grams. A silver disk having an approximate diameter of 0.49" and a thickness of approximately 0.1" weighs 2.62 grams. A gold implementation of the conductive button 138 is approximately 0.54" in diameter and has a thickness of approximately 0.1". The weight of the gold conductive button 138 is approximately 5.8 grams. Thus, a variety of different metals with slightly different dimensions and significantly different weights all produced similar test results. In these embodiments, the conductive button 138 is of sufficient size and weight to permit the manual positioning of the conductive button in proximity with the target cells.

At higher magnetic polarity frequencies, such as 1000 Hz-10,000 Hz, the physical dimensions and weight of the conductive button 138 may be reduced. For example, with 10,000 N and S poles on the disk 108 and motor speed of 7,200 rpm, the conductive button 138 in FIG. 6A may be less than 0.25" in diameter and weight less than 0.1 gram. Tests were satisfactorily conducted with the conductive button 138 being implemented by a circular copper disk (see FIG. 6A) with no central hole. The copper disk is approximately 0.17" in diameter and has a thickness of approximately 0.015". The copper disk weighed 0.005 grams. In yet another implementation, the conductive button 138 was implemented in the form of a square (see FIG. 6C) without a central hole. The square conductive button is copper and has dimensions of approximately 0.135"×0.135"×0.015" thick. The copper disk weighed approximately 0.005 grams. Those skilled in the art will appreciate that the smaller size conductive button 138 may be more suitable for implantation using conventional surgical techniques.

The conductive button in FIG. 6A may be implemented as a solid disk or may contain a through-hole 160. Those skilled in the art will appreciate that the through-hole 160 creates an opposite magnetic polarity to that of the remainder of the surface of the conductive button 138. For example, if the surface of the conductive button 138 is polarized as an N polarity, the through-hole 160 will be polarized as an S magnetic polarity. When the rotating magnetic field changes due to rotation of the magnetic rotor assembly 112 (see FIG. 1), the magnetic polarity of the surface of the conductive button and the magnetic polarity of the through-hole 160 both change polarities. Tests have indicated that the presence of the through-hole 160 increases the heating effect when the N and S magnetic fields collapse. Experiments have shown that temperature increase of approximately 15° F. can be achieved for a given magnetic field strength. That is, the temperature is greater with the through-hole 160 for a given magnetic strength of the magnets 110, a given rotational speed of the motor 102 and a given distance between the magnetic rotor assembly 112 and the conductive button 138.

Figure 6B:
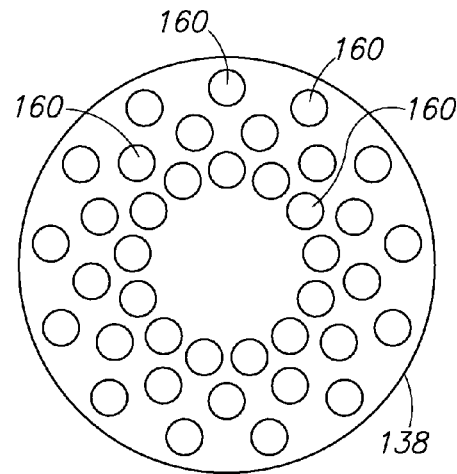

FIG. 6B illustrates the conductive button with a plurality of through-holes 160. In this embodiment, the multiplicity of through-holes 160 allow faster cooling of the conductive button 138 when the magnetic field is removed. Those skilled in the art will appreciate that the conductive button 138 in FIG. 6B has less mass than the conductive button 138 in FIG. 6A (assuming the buttons are made from the same material). The conductive button 138 of FIG. 6B may be useful in a treatment protocol in which the conductive button is heated to a very high temperature (e.g., 200° F.) for a short period and allowed to cool quickly. The patient may be exposed to a plurality of cycles of high temperature exposure for a short period of time followed by cooling.

Figure 6C:
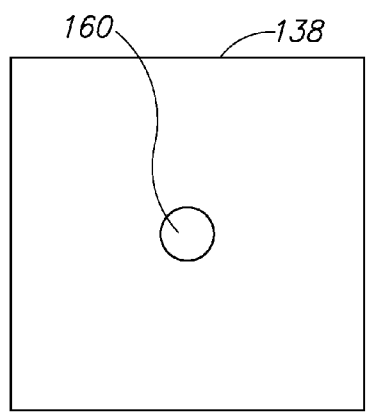
Figure 6D:
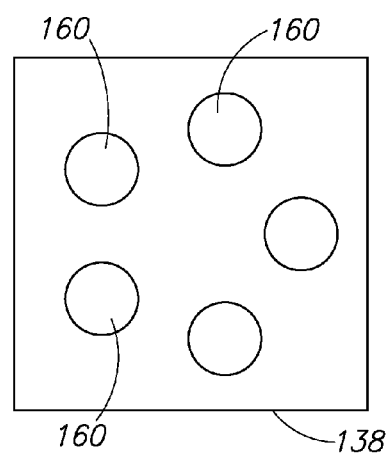

FIGS. 6C and 6D illustrate the conductive buttons 138 implemented in a square configuration. The conductive button of FIG. 6C has a single through-hole 160 while the conductive button of FIG. 6D contains a plurality of through-holes.

The physical size of the conductive buttons 138 may vary depending on the volume of tissue to be exposed to the hyperthermic treatment and the magnetic polarity frequency. The conductive buttons 138 used for insertion into the body are generally small enough in size to permit insertion using laparoscopic or other minimally invasive conventional surgical procedures.

The conductive buttons 138 in FIG. 6A-6D are shown in a top plan view. The conductive buttons 138 in FIGS. 6H-6L are shown in a side cross-section view. FIGS. 6E-6H show that a number of different physical structures may be used to implement the conductive button 138. For example, the conductive button 138 in FIG. 6F may be the side view of the conductive buttons illustrated in FIGS. 6A and 6C with a single through-hole 160. In contrast, the embodiments of FIGS. 6G and 6H illustrate an embodiment of the conductive button 138 with a central core 162 and multiple leaves 164 or layers extending therefrom. As those skilled in the art will appreciate, the multiple layers 164 create a greater surface area that is exposed to the magnetic field thus inducing greater eddy currents and more efficient heating of the conductive button. The embodiment of FIG. 6G also includes the through-hole 160 while the embodiment of FIG. 6H has no through-hole.

Figure 6E:
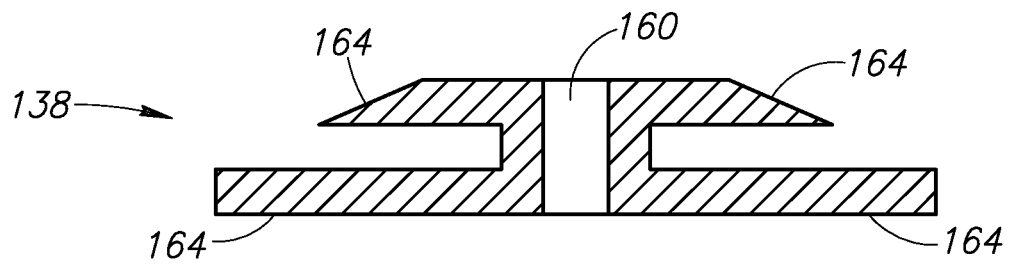
Figure 6F:
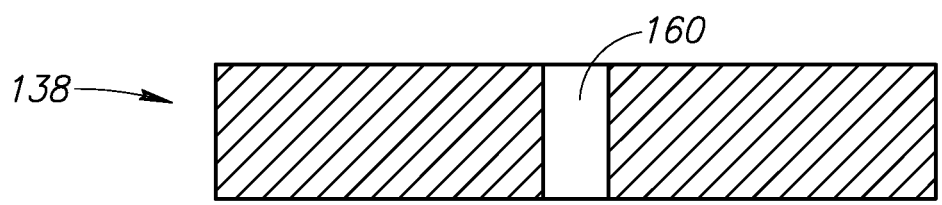
Figure 6G:
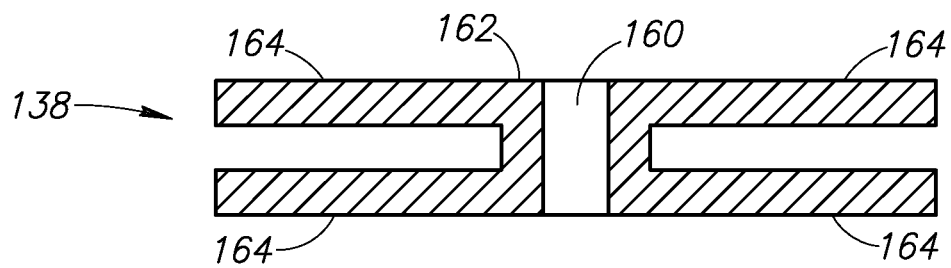
Figure 6H:
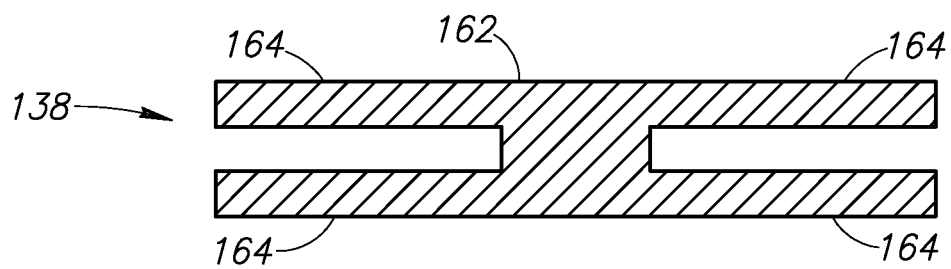
Figure 6I:
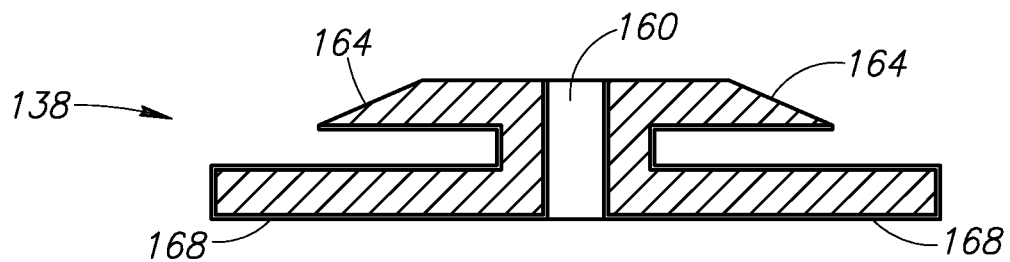
Figure 6J:
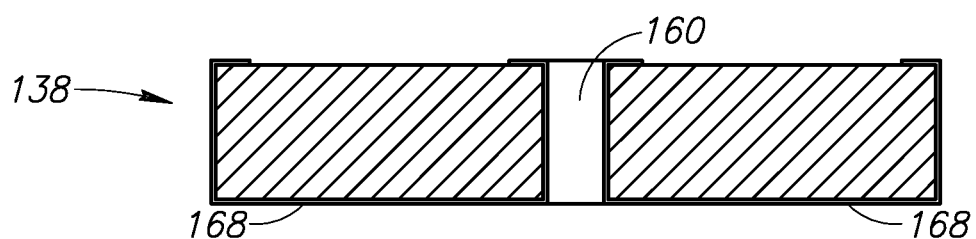
Figure 6K:
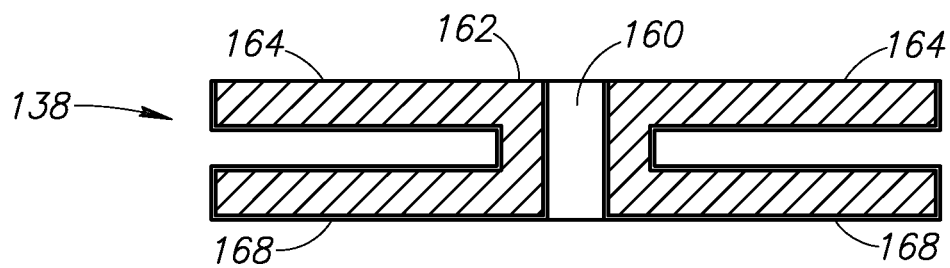
Figure 6L:
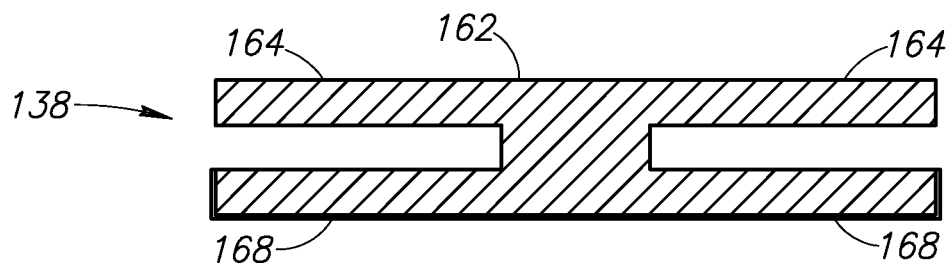

FIG. 6E illustrates a conductive button with multiple layers 164 and a through-hole 160. In the embodiment of FIG. 6E, one of the layers 164 is tapered. This embodiment may be useful for hyperthermic treatment of a tumor in which a specific area of the tumor is exposed to high temperatures generated by the conductive button 138.

The conductive buttons 138 are metallic and thus are good thermal conductors. When exposed to the magnetic field, the conductive buttons 138 achieve a homogeneous temperature and thus expose tissues in the body to a controlled homogeneous temperature. In some situations, it may be desirable to shield portions of the body from exposure to the homogeneous temperature. For example, a brain tumor may be positioned in the brain such that it is not possible to located the conductive button squarely within the center of the tumor to allow for homogeneous heating thereof. When placing the conductive button 138 near the tumor, it may be desirable to protect surrounding tissues from exposure to the hyperthermic temperatures created by the conductive button 138. The embodiments of FIGS. 6I-6L are identical to those of FIGS. 6E-6H, respectively, except that a portion of the conductive buttons 138 in FIGS. 6I-6L are covered with an insulating layer 168. The insulating layer 168 is a thermal insulator that protects surrounding tissues from exposure to the heat from the conductive button 138. FIGS. 6I-6L show only a few examples of the portions of the conductive button 138 that may be covered by the insulating layer 168. In operation, the conductive button 138 may have different arrangements of coverage of the insulating layer 168 or customized application of the insulating layer to generate more focused non-homogeneous heat. A number of different bio-compatible materials can be used to form the insulating layer 168. Medical grade PTFE Green 8-403P coatings, nylon, Teflon, Teflon S, FEP, along with PFA materials are found to be satisfactory to implement the insulating layer 168. The insulation can be applied as a single layer or built up using multiple layers of coatings. The thickness of the coating of the insulating layer 168 depends on the insulation properties of the selected material. However, the selection of different materials for the insulating layer 168 and the thickness of the insulating layer are design choices that can be satisfactorily made by one of ordinary skill in the art using the teachings contained herein.

Those skilled in the art will appreciate that maximum exposure to the magnetic field occurs when the flat side of the conductive button 138 is aligned at approximately 90° with respect to the magnetic field. A co-axial magnetic flux relationship between the magnetic rotor assembly 112 and the conductive button 138 provide the greatest induction of eddy currents when the conductive button is oriented to be in the center of the poles of the magnets 110. As noted above, the range of the distances between the magnetic rotor assembly 112 and the conductive button 138 may be as little as 0.3" to greater than 6.0". Magnetic flux densities required to induce homogeneous heat in the conductive button 138 has been observed as low as 200 gauss with a 1" air gap and tested to over 1,500 gauss. In a situation where the flat surface of the conductive button 138 is not precisely aligned with the magnetic poles, there will still be heat induced by eddy currents on the surface of the conductive button, but they may be at a reduced level. Use of the thermocouple 142 (see FIG. 3) or other temperature monitoring device can be used with the controller 144 to adjust the position of the magnetic rotor assembly 112 to compensate, at least partially, for the non-alignment.

Tests have been conducted and found that the conductive buttons 138 may be manufactured from a variety of different electrically conductive metals. Tests have been conducted using gold, silver, aluminum, and copper with satisfactory results. Other metals may also be used. The conductive buttons 138 are not limited by the specific metal used in the manufacture. Metal alloys may also be used satisfactorily with the system 100.

Figure 7:
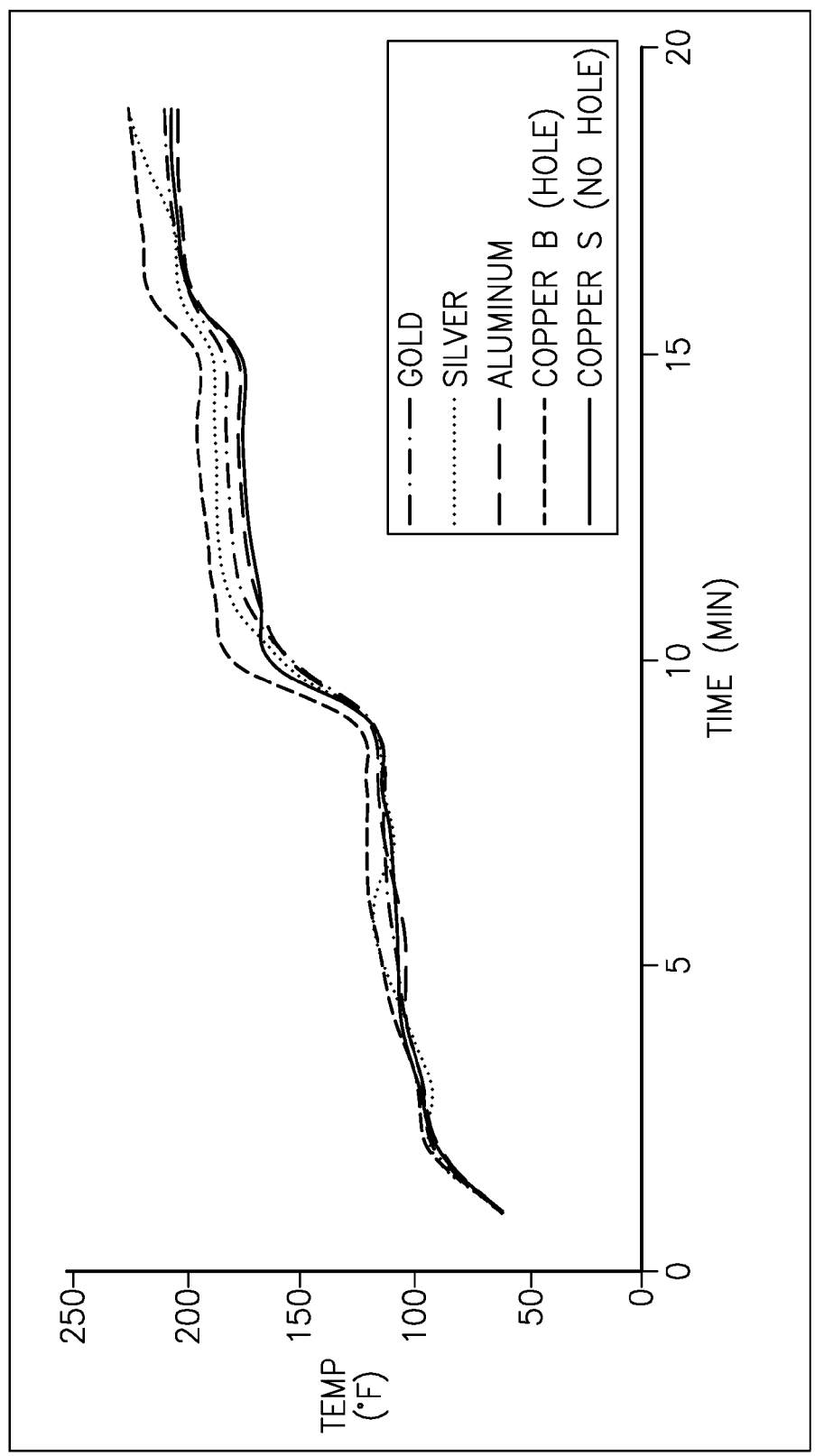
FIG. 7 is a chart illustrating temperature versus time for a variety of different metals used to implement conductive buttons in the system of FIG. 1.

Those skilled in the art will appreciate that the conductive materials may have a different rate of temperature change. FIG. 7 illustrates a graph of temperature over a period of time for gold, silver, aluminum, and two implementations with copper. One implementation is a copper conductive button 138 with no through-hole while another copper implementation uses a through-hole. As can be seen from FIG. 7, the rate of change of temperature between 50° F. and 100° F. is similar for all samples. In the initial test, the conductive button 138 was placed at a predetermined distance from the magnetic rotor assembly 112 shown in FIG. 1. At approximately time T equals 9 minutes, the distance between the magnetic rotor assembly 112 and conductive button 138 was decreased to thereby generate an increase in temperature. As can be seen from FIG. 7, the copper embodiment of the conductive button 138 with the through-hole 160 reacts most quickly and achieves a higher overall temperature with all other parameters remaining constant. That is, the copper conductive button 138 with the through-hole 160 displays the fastest rate of increase and achieves the highest temperature for a given distance between the magnetic rotor assembly 112 and the conductive button. Copper is also relatively inexpensive. While copper may be considered toxic at high levels, the copper conductive button 138 is only present in the body for a short period of time thus minimizing any exposure and risk of copper toxicity. Alternatively, the copper conductive button 138 may be coated with a protective layer of a nontoxic metal, such as gold.

As discussed above, the conductive button 138 may also be implemented as a collection of metallic nanoparticles. In an exemplary embodiment, the metallic nanoparticles are chemically bonded to antibodies that will preferentially attach to the target tissue. That is, the antibodies will form a bond with features on the cell surface of the target tissue, such as tumors, and allow the magnetic particles to accumulate at the treatment site. Subsequent exposure to high magnetic polarity frequencies (e.g., >1.0 MHz) will heat the accumulated metallic nanoparticles and cause heating or ablation of the target tissues.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

The invention claimed is:

1. A system for hyperthermic treatment of target cells, comprising:
   a non-magnetic metallic object positionable in proximity with the target cells to be hyperthermically treated;
   a motor having a rotatable motor shaft extending therefrom;
   a plurality of permanent magnets coupled to an end of the motor shaft and configured to rotate with the motor shaft;
   a positioning mechanism to place the rotating magnets into position at a first distance from the metallic object wherein the metallic object is heated to a first temperature by exposure to a rotating magnetic field generated by the permanent magnets as they rotate with the motor shaft, the rotating magnetic field acting to induce eddy currents on a surface portion of the metallic object.

2. The system of claim 1 wherein the metallic object has sufficient size and weight to permit the manual positioning of the metallic object in proximity with the target cells.

3. The system of claim 2 wherein the metallic object weighs between 0.005 and 6.0 grams.

4. The system of claim 1 wherein the metallic object comprises a plurality of metallic nanoparticles that accumulate in a region surrounding the target cells prior to exposure to the rotating magnetic field.

5. The system of claim 4 wherein the metallic object comprises a plurality of metallic nanoparticles having a protein binding component attached thereto, the protein binding component attaching to the target cells.

6. The system of claim 4 wherein the rotating magnetic field generated by the permanent magnets as they rotate with the motor shaft has a magnetic polarity frequency of greater than 1 megahertz.

7. The system of claim 4 wherein the motor is configured to rotate at more than 7,000 revolutions per minute and the plurality of permanent magnets is in the range of 1,000 to 20,000 permanent magnets.

8. A method for hyperthermic treatment of a tumor comprising:
positioning a non-magnetic metallic object in a location proximate the tumor;
positioning a plurality of permanent magnets coupled to an end of a motor into position at a first distance from the metallic object; and
rotating the permanent magnets by rotating the motor to thereby generate a rotating magnetic field; and
exposing the metallic object to the rotating magnetic field generated by the permanent magnets as they rotate with the motor shaft to thereby heat the metallic object to a first temperature by exposure to the rotating magnetic field, the rotating magnetic field acting to induce eddy currents on a surface portion of the metallic object.

9. The method of claim 8 wherein positioning the plurality of permanent magnets comprises positioning a disk having a plurality of magnetized regions having alternating magnetic polarities.

10. The method of claim 8 wherein the motor is a variable speed motor, the method further comprising operating the motor at a first speed.

11. The method of claim 10, further comprising operating the motor at a second speed greater than the first speed to thereby increase heating of the metallic object to a second temperature greater than the first temperature.

12. The method of claim 10, further comprising operating the motor at a second speed less than the first speed to thereby decrease heating of the metallic object to a second temperature less than the first temperature.

13. The method of claim 8, further comprising positioning the rotating magnets into position at a second distance from the metallic object less than the first distance to thereby increase heating of the metallic object to a second temperature greater than the first temperature.

14. The method of claim 8, further comprising positioning the rotating magnets into position at a second distance from the metallic object greater than the first distance to thereby decrease heating of the metallic object to a second temperature less than the first temperature.

15. The method of claim 8, further comprising positioning a temperature probe in proximity with the metallic object to provide temperature data indicative of the temperature of the metallic object.

16. The method of claim 15, further comprising using the temperature data to maintain the temperature of the metallic object substantially at the first temperature.

17. The method of claim 16 wherein maintaining the temperature of the metallic object comprises adjusting the position of the rotating magnets to maintain the temperature of the metallic object substantially at the first temperature.

18. The method of claim 16 wherein the motor is a variable speed motor and maintaining the temperature of the metallic object comprises adjusting the motor speed to maintain the temperature of the metallic object substantially at the first temperature.

19. The method of claim 15, further comprising using the temperature data to adjust the temperature of the metallic object between the first temperature and a second temperature different from the first temperature.

20. The method of claim 8 wherein the metallic object has sufficient size and weight to permit the manual positioning of the metallic object in proximity with the target cells.

21. The method of claim 20 wherein the metallic object weighs between 0.005 and 6.0 grams.

22. The method of claim 8 wherein the metallic object comprises a plurality of metallic nanoparticles that accumulate in a region surrounding the target cells prior to exposure to the rotating magnetic field and positioning the metallic object comprises injecting the metallic nanoparticles into the patient.

23. The method of claim 22 wherein the metallic object comprises a plurality of metallic nanoparticles having a protein binding component attached thereto, the protein binding component attaching to the target cells.

24. The method of claim 22 wherein the rotating magnetic field generated by the permanent magnets as they rotate with the motor shaft has a magnetic polarity frequency of greater than 1 megahertz.

25. The method of claim 22 wherein rotating the motor comprises rotating the motor at more than 7,000 revolutions per minute and positioning the plurality of permanent magnets comprises positioning 1,000 to 20,000 permanent magnets into position at the first distance.

26. The system of claim 1, further comprising a metal plate coupled to the end of the motor shaft and configured to rotate therewith wherein the plurality of permanent magnets are mounted on one side of the metal plate spaced apart from each other and proximate a peripheral edge of the metal plate.

* * * * *